March 5, 1974 R. H. McCOLLEY Plant Pat. 3,502
DISTINCT VARIETY OF PHILODENDRON PLANT
Filed April 10, 1972
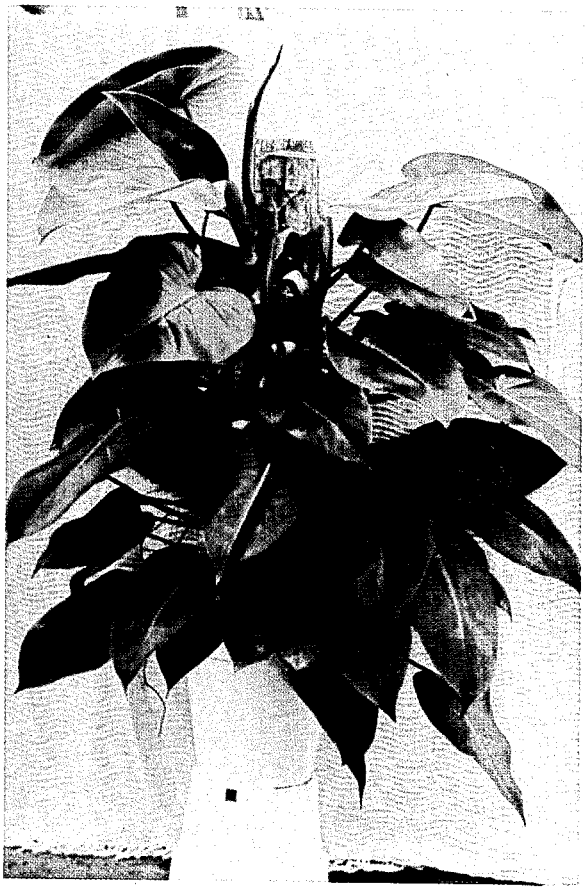

United States Patent Office

Plant Pat. 3,502

Patented Mar. 5, 1974

3,502

PHILODENDRON PLANT

Robert H. McColley, P.O. Box 17126, Orlando, Fla. 32810

Filed Apr. 10, 1972, Ser. No. 242,846

Int. Cl. A01h *5/00*

U.S. Cl. Plt.—88 1 Claim

ABSTRACT OF THE DISCLOSURE

The disclosure hereof is of a Philodendron plant particularly characterized by the contrasting red and green colors of the leaves in immature and mature state, the dark red color of the sheath covering as the leaf opens, the sheath curling back hanging on to the stem for long periods of time, together with superior disease resistance to bacterial soft rot and shot-gun fungus.

DESCRIPTION OF THE INVENTION

The instant invention relates to a new and distinct variety of Philodendron which was hybridized by me in the vicinity of Orlando, Fla.

The seedling which is the result of an extensive breeding program which I have conducted and which I carry on, was selected and developed from a cross in which the female parent was a seedling also bred and selected by me, whose parentage included *Philodendron hastatum, erubescens, wendlandii, imbe* and an unidentified species not generally known in the trade, the female parent being well known in the trade, although none of these particular species is patented.

The male parent was also bred and selected by me, and is well known in the trade, being a cross between two unidentified species, one of the latter being the same as the unidentified species in the female parent.

There is thus a rather large number of distinct Philodendron species involved in the cross, which has resulted in the hybridization of my new variety. The cross resulting in the instant species may be said to derive specifically from a seedling selected from a group that was the result of using Philodendron Burgundy as a female parent and Philodendron Emerald Queen as a male parent.

Asexual propagation of my new variety has been accomplished by tip cuttings, including the removal and rooting of terminal shoots of three or more leaves. Other methods of propagation have been resorted to, including single eye cuttings, air layering and the use of plunged cane length cuttings.

My new variety is distinctively different from both of its parents or any other Philodendron presently known to me.

My new variety is highly resistant to bacterial soft rot, a disease very prevalent in the Florida and Gulf Coast areas. It is also resistant, virtually immune, to the so-called "shot-gun" fungus, which is rather common dehydration problem.

My new variety brings to the trade brilliant colors not available before the leaf itself being a brilliant green with stem and petioles of dark red. In addition to this color, the sheath covering of each new leaf is dark red, curls back as the leaf unfolds and remains on the plant for months.

The general impression provided therefore is a group of dark red curls attached to the stem of the plant.

Insofar as I am aware, no flowers of my new variety have ever been observed, and it is known that flowering of this type of Philodendron is very sparse. Flower initiation and development would require ideal environmental conditions with plants at fu'l maturity, and no real attempt has been made to develop the same.

My new variety is a climber, and when plants of eight leaves or over are involved, these plants will thus require normal staking.

The rate of growth may be termed medium; undernormal greenhouse conditions a young plant developing in three or four months from a tip cutting. It may require six to eight months to produce a mature plant from the same type of cutting.

My new variety is vigorous, compact and non-branching. An average plant of five leaves propagated from a tip cutting may attain a height of twelve inches and a spread of 18 to 20 inches. A five-leaved plant propagated from a single eye cutting will attain a height of eight inches, with a spread of 12 to 15 inches.

The detailed observations from which the following description is made were taken in my greenhouse in Orlando, Florida. As will be readily understood by those skilled in the art, significant variation may occur in accordance with various environmental conditions including temperature, humidity, day length, and available nutrients, but where the conditions are consistent, the plants are consistent and run true to form.

My new variety has been found to retain its distinctive characteristics through successive asexual reproduction.

The accompanying drawing forming a part hereof, discloses a typical plant of my new variety, the color being as nearly true as possible, with color illustrations of this type. Color references are made to Nickerson Color Fan published by Munsell Color Company, with observations being recorded by daylight illumination under vinyl of not more than 30% shade. Comparison and/or contrast may be readily made with the variety of my patented Philodendron plant disclosed in Plant Pat. No. 3,034 dated Mar. 2, 1971, the general differences residing in the substantially greater impression of dark red and contrasting colors of leaves.

(I) Form characteristics

| | |
|---|---|
| (1) Leaf shape: | |
| (a) Mature | Ovate. |
| (b) Immature | Do. |
| (c) Tip | Acute. |
| (d) Base: | |
| (1) Mature | Auriculate. |
| (2) Immature | Obtuse to cordate. |
| (e) Displacement | Smooth. |
| (f) Margin | Entire. |
| (g) Veination | Raised midrib. Sunken veins. |
| (2) Leaf attachment | Stalked. |
| (3) Leaf arrangement | Alternate. |
| (4) Petiole | Medium to short. |
| (5) Stem | Short to 2". |
| (6) Overall appearance | Dense. |

(II) Size characteristics of typical commercial size plant

| | Inches |
|---|---|
| (1) Leaf itself: | |
| (a) Width—widest point | 4 to 7 |
| (b) Width—1" from tip | 1½ |
| (c) Length | 6 to 10½ |
| (d) Thickness | .016 to .019 |
| (2) Petiole length | 4 to 8 |
| (3) Internode spacing | 1 to 2 |
| (4) Stem diameter | ⅜ to ¾ |

(III) Color characteristics

| | |
|---|---|
| (1) Leaf (mature): | |
| (a) Top | 5GY 4/3 |
| (b) Bottom | 5GY 5/6 |
| (c) Margin | 2.5R 3/7 |

(2) Leaf (immature):
- (a) Top ..... 5GY 7/10
- (b) Bottom ..... 5R 6/11
- (c) Margin ..... 2.5R 4/10

(3) Leaf midrib:
- (a) Top ..... 2.5R 5/12
- (b) Bottom ..... 2.5R 3/7

(4) Leaf veins:
- (a) Top ..... 2.5R 5/12
- (b) Bottom ..... 2.5R 3/7

(5) Stem and petiole ..... 2.5R 3/7

(6) New leaf sheath covering ..... 5R 3/7

I claim:

1. A new and distinct variety of Philodendron plant substantially as herein disclosed, characterized as to novelty by its superior growth, resistance to shot-gun fungus and bacterial soft rot, dark red and green color contrasts in immature and mature leaves, the dark red color of the sheath covering with its tendency to curl back and hang on to the stem for long periods of time.

No references cited.

ROBERT E. BAGWILL, Primary Examiner